US005782870A

United States Patent [19]

McAfee

[11] Patent Number: 5,782,870

[45] Date of Patent: Jul. 21, 1998

[54] FOOT PLATE CONTROL MECHANISM FOR CHIROPRACTIC TABLE

[75] Inventor: Brent McAfee, Lisbon, Iowa

[73] Assignee: Lloyd Table Company, Lisbon, Iowa

[21] Appl. No.: 692,632

[22] Filed: Aug. 6, 1996

Related U.S. Application Data

[60] Provisional application No. 60/002,112 Aug. 10, 1995.

[51] Int. Cl.$^{6}$ .............................. A61F 5/00; A61G 7/005; A61G 7/05

[52] U.S. Cl. .............................. 606/244; 5/610

[58] Field of Search .............................. 5/610, 611, 624; 606/242, 243, 244

[56] References Cited

U.S. PATENT DOCUMENTS

| | | | |
|---|---|---|---|
| 1,735,703 | 11/1929 | Williams | 606/244 |
| 1,989,434 | 1/1935 | Thompson | 606/244 |
| 2,381,922 | 8/1945 | Norris | 606/244 |
| 4,271,830 | 6/1981 | Moon | 606/244 |

*Primary Examiner*—Alexander Grosz
*Attorney, Agent, or Firm*—James C. Nemmers

[57] ABSTRACT

A mechanism for controlling the raising and lowering of the foot plate on a chiropractic table of the tilt-elevating type. The foot plate is pivotly mounted on the fixed base and has stabilizer pins that are engaged by lugs on the upper or moveable part of the table when the table is tilted and disengaged when the table is returned to a horizontal position. A sliding bar and roller mechanism slowly lowers the foot stand to its normal position on or near the floor.

4 Claims, 3 Drawing Sheets

FOOT PLATE CONTROL MECHANISM FOR CHIROPRACTIC TABLE

This application claims the benefit of U.S. Provisional Application No. 60/002.112 filed Aug. 10, 1995. Applicant previously filed with said Provisional Application a verified statement claiming small entity status and such status still exists, is proper and is desired. Applicant therefore requests that small entity status be granted and a copy of the verified statements filed in the Provisional Application are attached and accompany this nonprovisional application.

BACKGROUND OF THE INVENTION

Chiropractic tables have long been used by doctors of chiropractic to perform various examinations, adjustments and procedures on patients. The tables commonly are provided with various fully adjustable head, chest, lumbar and pelvic sections, and frequently employ a scissors-type elevation mechanism that allows the table to be raised and lowered to a convenient height for the various procedures and manipulations. In addition, some tables have a tilting feature in which the head portion of the table can be tilted to an almost vertical position. These tables with a tilt feature are provided with a foot stand or foot plate upon which the patient's feet rest when the table is tilted. Some tables have only the tilting feature while others are elevating tables only, and other tables combine both the tilting and elevating features.

In the tables that have the tilting feature, the foot plate or foot stand is normally resting in a horizontal position on or near the floor so as to be out of the way when not in use. However, when the table is tilted from a horizontal to a more vertical position, the foot plate is raised so as to support the feet of the patient as the table is tilted. When the table is lowered back to a horizontal position, the foot plate is automatically lowered to its position on the floor.

However, in tables that combine the tilt feature with the capability of elevating the table, the foot plate of necessity must be attached to the upper part of the table which is raised and lowered and tilted. In tables of this type, the foot plate protrudes out from the upper part of the table when it is in a horizontal position and the foot plate is not in use because the foot plate is fixed to the upper or elevating part of the table. As the table is tilted, the foot plate will be in the proper position to support the feet of the patient. However, having the foot plate protrude from the foot end of the table when it is in a horizontal position and the foot plate is not in use, is inconvenient and can interfere with the efficient performance of other procedures. It therefore would be a very desirable feature in a tilt-elevating type of table to have the foot plate on the floor at all times except when the table is tilted at which time it would be raised to support the feet of the patient. There is however no known structure by which this desirable feature can be accomplished.

It is therefore an object of the invention to provide a tilt-elevating type chiropractic table having a foot plate that will automatically be engaged and supported when the table is tilted from a horizontal position and which foot plate will automatically be returned out of the way to a position on the floor when the table is returned to a horizontal position.

SUMMARY OF THE INVENTION

The invention provides a mechanism by which a pivotly mounted foot plate has a pair of stabilizer pins that are engaged by correspondinglugs at one end of the upper part of the tilting-elevating table. When the lugs engage the pins, they provide a pivot for the foot plate and a connection with the upper part of the table so that a sliding bar and roller arrangement can raise the foot plate into the proper position as the table tilts. This sliding bar and roller arrangement will also prevent the foot plate from dropping suddenly as the table is tilted back to a horizontal position and the stabilizer pins become disengaged from the lugs on the upper part of the table.

BRIEF DESCRIPTION OF THE DRAWING

FIG. 4A is an end elevational view of the foot end of the table shown in FIG. 2A.

DESCRIPTION OF THE PREFERRED EMBODIMENT OF THE INVENTION

Chiropractic tables are available in many types and designs. In the simpler versions, a stationery base supports moveable and adjustable head, chest, lumbar and pelvic or ankle sections. Movement of the individual sections can be manually controlled or can be controlled by electrohydraulic or pneumatic systems. In tables of this type, no foot plate is necessary or used.

Because the height of the table can be important during certain examinations or procedures, and because height is also important for the comfort of the chiropractic physician and will lessen his or her fatigue, tables are known and available in which the upper portion of the table that supports the moveable and adjustable sections can also be raised and lowered usually on a scissors-type linkage with electrohydraulics or a magnetic actuator providing the power to raise and lower and control elevation of the table.

Other tables have a fixed predetermined height with moveable and adjustable sections for the patient's head, chest, etc., but these tables also have a tilt feature in which the entire upper frame that supports the individually adjustable sections can be tilted to an infinite number of positions from horizontal to 70° from vertical, for example. These tilting tables utilize a foot plate that has a fixed connection with the upper frame so that the foot plate will be tilted as the upper portion tilts but will be lowered back to a horizontal position on or near the floor so that it will be out of the way when the table is returned to a horizontal position.

There are also available tables which combine all of the foregoing described features of elevation and tilt, along with the individually moveable and adjustable sections supported on an upper frame that is raised, lowered and tilted. In tables of this type, the foot plate is permanently engaged with and attached to the upper frame so that the foot plate raises and lowers with the upper frame. In these table, the foot plate also tilts to support the feet of the patient when the upper frame is tilted. However, since the foot plate is on a fixed pivot and attached to the upper frame, it protrudes from the upper frame and can interfere with certain procedures.

Figure 1:
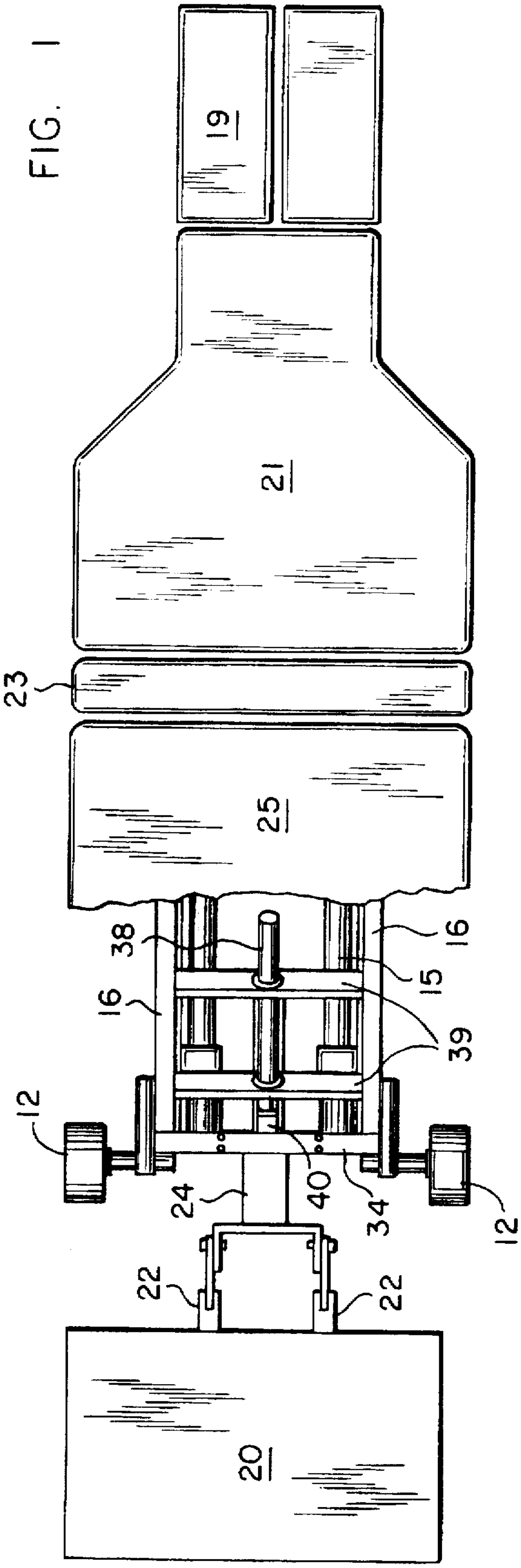
FIG. 1 is a top or plan view of a tilt-elevating type chiropractic table with a portion of the upper patient supporting structure broken away.
Figure 2:
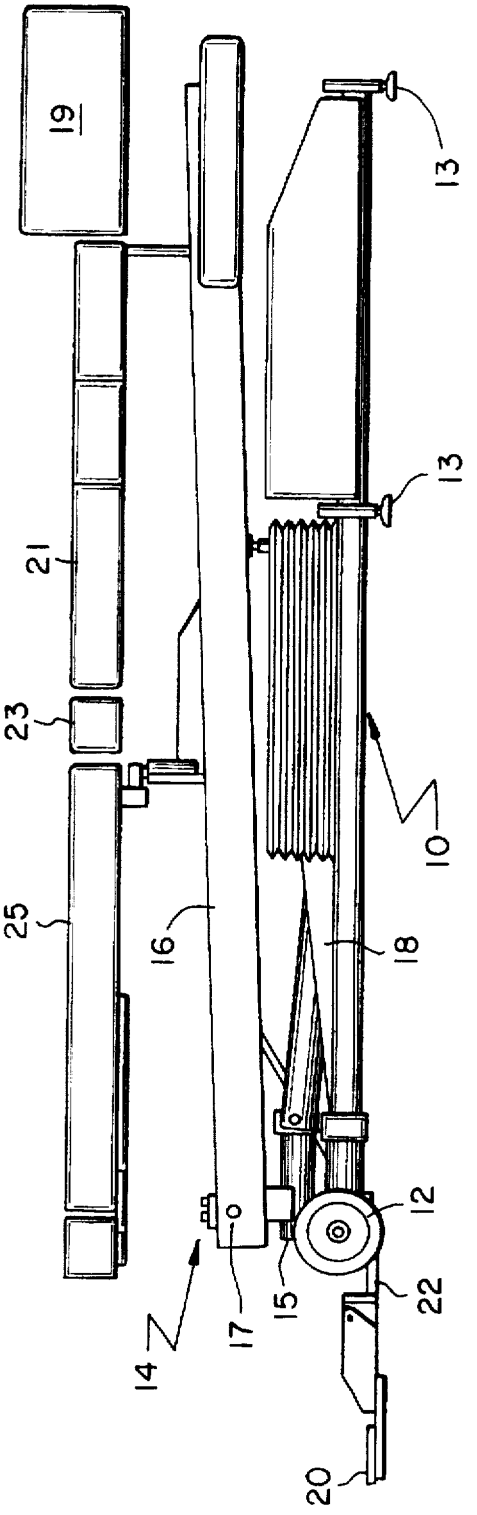
FIG. 2 is a side elevational view of a tilt-elevating type table and and showing the table in its lowered position.

Each of the figures in the drawings have portions of the structure broken away so as to more clearly illustrate certain features. In FIGS. 1 and 2 of the drawings, there is illustrated a chiropractic table which incorporates the principles of the invention. The table illustrated is of the tiltelevating type, but the mechanisms for raising and lowering the table and tilting it have not been fully illustrated since these are well known to those skilled in the art. Also, the various individually moveable and adjustable sections carried by the upper frame have not been shown in great detail. As is well known to those skilled in the art, the basic table includes a base frame 10 that is stationery and is supported at the foot end on a pair of wheels 12. This allows the table to be moved if desired. Commonly, the opposite or head end of the base frame 10 has fixed supports 13 so that the table will not inadvertently move during an examination or procedure.

The table also has an upper supporting assembly indicated generally by the reference numeral 14. This assembly 14 commonly includes a pair of longitudinally extending and spaced apart frame members 16 to which there can be attached the individually moveable and adjustable head 19, chest 21, lumbar 23 and pelvic 25 sections. The base frame 10 and upper supporting assembly 14 also are used to support the various controls and the electrical-hydraulic system that powers and controls the various movements of the table. Commonly, the upper supporting assembly 14 is supported on the base frame 10 by pivotal connection of a scissors-type linkage 18 to upper frames 15, which are longitudinally extending members to which the frame members 16 are pivotally connected by pins 17. The scissors-type linkage 18 and frames 15 provide for the upper supporting assembly 14 to be raised or lowered by hydraulic cylinder 11 in a way that the assembly will remain substantially horizontal and parallel to the base frame 10 unless the frame members 16 are tilted as described hereinafter.

Although not completely shown, the mechanism for tilting the upper supporting assembly 14 from a horizontal to a more vertical position, say 70° from the vertical, is well known to those skilled in the art and consists of a mechanical linkage arrangement 27 (see FIG. 5) that allows the head end of the upper supporting assembly 14 to be raised while the foot end is lowered. Tilting is accomplished by any suitable power means, such as a hydraulic cylinder 29 (see FIG. 5).

Figure 4A:
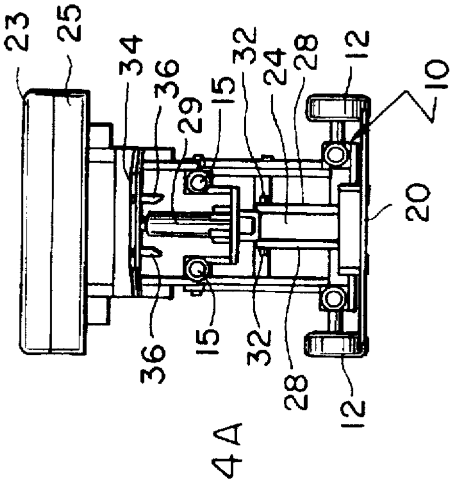
FIG. 4A is a side elevational view similar to FIG. 2 but showing the table with the patient support position elevated.
Figure 4:
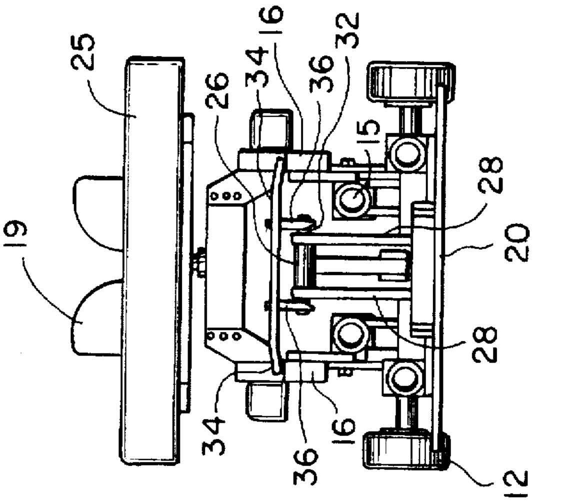
FIG. 4 is an end elevational view of the foot end of the table shown in FIG. 2A.
Figure 3:
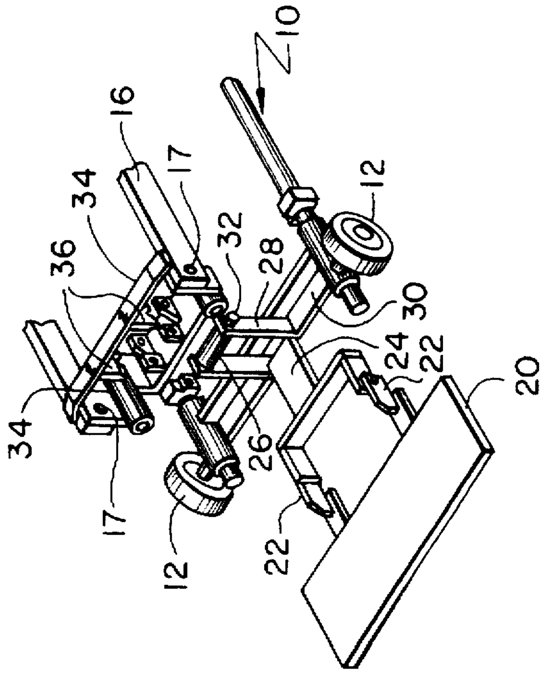
FIG. 3 is a perspective view of a portion of the foot end of the table of FIGS. 1 and 2 with some components removed to illustrate the mechanism for controlling movement of the foot plate.

In a table utilizing the tilt feature, the table is provided with a foot plate 20 mounted on a pair of supporting arms 22 that are connected to an L-shaped member 24, the upper end of which is solid and is mounted for pivotal movement about a pivot point 26 between a pair of spaced apart vertically extending supports 28. The supports 28 are affixed to a cross member 30 that forms a part of the base frame 10, as best seen in FIGS. 3 and 4. A stabilizer pin 32 provides for pivoting of the foot plate 20 at pivot point 26, and the pin 32 extends outwardly beyond the supports 28, as best seen in FIG. 3.

Forming a part of the upper supporting assembly 14 and connected to the longitudinally extending frame members 16 are a pair of inwardly extending arms 34 joined at their inner end.

Each of the arms 34 has formed at its inner end a downwardly extending lug 36 that provides a slot of a width to engage over and around the stabilizer pins 32. These lugs 36 thus are engageable with the pins 32 when the linkage that tilts the upper supporting assembly 14 is moved to tilt the table. The pivot point 26 then becomes the pivot point of the upper assembly 14, the pins 17 being on a common axis with the pins 32 when the lugs 36 are engaged. As the upper supporting assembly 14 tilts, the lugs 36 will be lowered and aligned with the pins 32 so that they engage the pins 32 to provide a solid support and connection of the upper supporting assembly 14 with the foot plate 20.

Figure 2A:
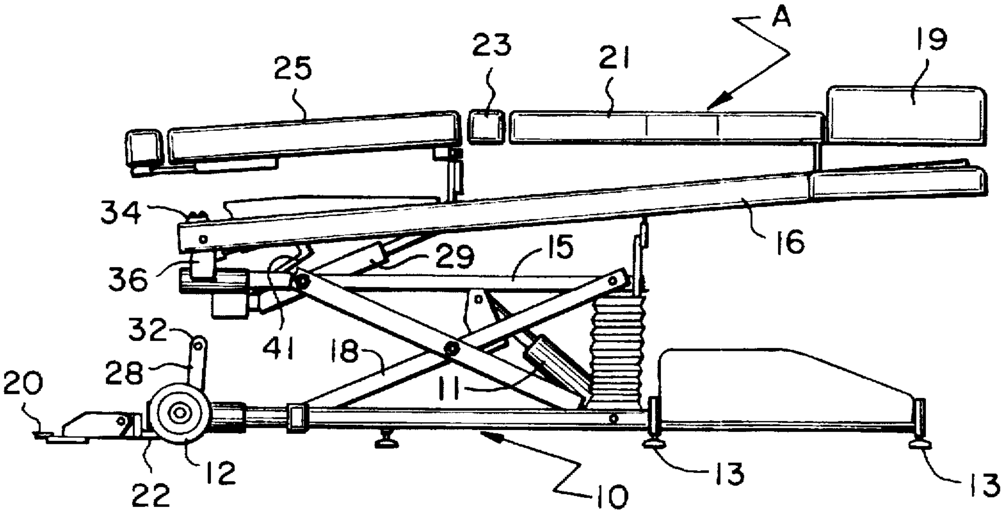
Figure 5:
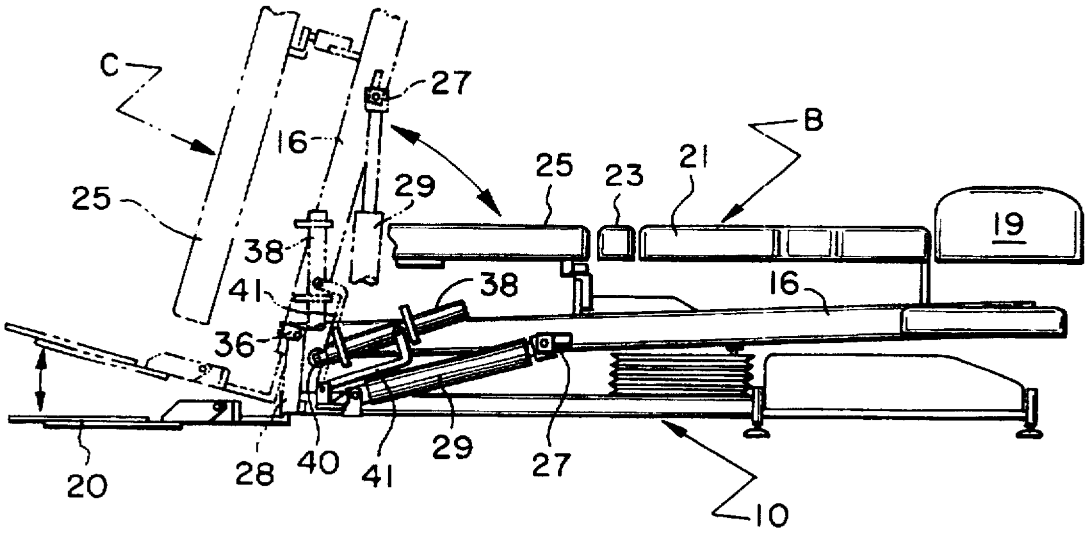
FIG. 5 is a side elevational view showing the patient support portion in a lower position and in a tilted position.

In order to tilt the foot plate 20 into the proper position and also to allow it to return to its horizontal position when the upper supporting assembly 14 is lowered to a horizontal position, there is mounted between the frame members 16 of the upper supporting assembly 14 a slidable bar or plunger 38 that has a roller 40 attached to its outer end. Bar 38 is slidable in cross members 39 that are attached to the frame nembers 16. An L-shaped link 41 has its lower end pivotally attached to the upper frame 15 and its upper end attached to the bar 38 (see FIG. 2A and 5). As the bar 38 is extended due to the link 41 as the upper assembly 14 tilts, the roller 40 that is engaged with the solid rear vertical portion of the Lshaped member 24 that supports the foot plate 20, will force the foot plate 20 to pivot about pivot point 26 thus tilting the foot plate 20 upwardly as the upper supporting assembly 14 is tilted upwardly toward a more vertical position. FIG. 2A and 5 illustrates this and show the upper supporting assembly 14 in a horizontal elevated position "A" with the lugs 36 disengaged from the pins 32 and the foot plate 20 in a horizontal position resting on or near the ground. When the upper supporting assembly 14 is to be tilted, it is first lowered to horizontal position "B" shown in FIG. 2, and then the tilt mechanism actuated to start moving the head end of the upper supporting assembly 14 toward a more vertical position. In FIG. 5, position "C" shows the upper supporting assembly 14 in a common tilted position. As illustrated in FIG. 5, the roller 40 is extended outwardly by action of the link 41 to pivot the foot plate 20 to the proper position. When the upper supporting assembly 14 is lowered back to a horizontal position, the action of the components is the reverse of those just described. With the foot plate 20 returned to its position on the floor it is thus out of the way of the practitioner for other procedures to be performed with the table in the horizontal position.

From the foregoing description, it will be understood by those skilled in the art that the invention provides a way of automatically lowering the foot plate out of the way and onto the floor when it is not necessary for use. The combination of components that comprise the invention provide an automatic means for tilting the foot plate 20 when the table is tilted toward the vertical and providing support for the patient at all times while the table is tilting. All the practitioner has to do is to actuate the controls, usually foot pedals, commonly provided with tables of this type to tilt the table, and the foot plate will be automatically pivoted upwardly to the proper position. The invention thus provides a way of automatically positioning the foot plate for use when the table is tilted and automatically returning it out of the way when the table is not tilted. This is a great advantage to the practitioner who need not have a foot plate in the way of practicing other procedures with the table in the horizontal position. This thus allows the practitioner to conduct the examinations and procedures in a more efficient manner.

What is claimed is as follows:

1. A foot plate attachment for use in combination with a chiropractic table of the tiltable type having a base supporting an upper patient-support portion that is normally generally horizontal but is tiltable relative to the base and which upper patient-support portion includes frame members that extend longitudinally from the head end to the foot end of the table, the upper patient-support portion supporting adjustable sections used in chiropractic procedures, said foot plate attachment comprising: a foot plate pivotly mounted on the base and normally positioned on or near the floor at the foot end of the table when the upper patient-support portion is generally horizontal, lugs having slots therein secured to the frame members of the upper patient support portion of the table near the foot end, stabilizer pins connected to the foot plate and engageable with the slots in the lugs when the patient-support portion is tilted with the foot end downwardly and which pins are disengaged from the lugs as the said portion is returned to a normal horizontal position, and means for controlling the raising and lowering of the foot plate when the lugs engage with and disengage from the stabilizer pins and the patient-support portion tilts and then returns to its normal horizontal position.

2. The foot plate attachment of claim 1 in which said means includes an extendible bar and roller mechanism combined with the frame members of the upper patient-support portion and which roller is engageable with the foot plate to raise the foot plate into the proper position as the table tilts and the bar and roller extend and to slowly lower the foot plate to its normal position on or near the floor when the patient-support portion returns to its horizontal position.

3. The foot plate attachment of claim 2 in which the stabilizer pins are located at the pivot point of the foot plate and a link is pivotly connected at one end to the base and the other end is connected to the extendible bar so that the link causes the bar to extend as the table tilts.

4. The foot plate attachment of claim 3 in which the foot plate is connected to an L-shaped support having an upper vertically extending leg that is pivotly connected to the base and a lower horizontally extending leg to which the foot plate is connected, the roller of the bar and roller mechanism being engageable with the upper leg of the L-shaped support.

* * * * *